(12) United States Patent
Eastman et al.

(10) Patent No.: US 6,767,997 B2
(45) Date of Patent: Jul. 27, 2004

(54) ANTIBODIES THAT BIND DEOXYRIBONUCLEASE IIβ ENZYME PROTEINS

(75) Inventors: Alan Richard Eastman, Hanover, NH (US); Ronald Joe Krieser, Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 177 days.

(21) Appl. No.: 09/949,434

(22) Filed: Sep. 7, 2001

(65) Prior Publication Data

US 2002/0028495 A1 Mar. 7, 2002

Related U.S. Application Data

(60) Division of application No. 09/574,942, filed on May 19, 2000, which is a continuation-in-part of application No. 09/541,840, filed on Apr. 3, 2000, now Pat. No. 6,350,723.

(51) Int. Cl.$^7$ .............................................. C07K 16/00
(52) U.S. Cl. ................................................. 530/388.26
(58) Field of Search .................................... 530/388.26

(56) References Cited

PUBLICATIONS

Stryer et al, in Biochemistry, Third edition, W H Freeman Company, New York, pp. 31–33, 1998.*
Ngo et al, 1994, The Protein Folding Problem and Tertiary Structure Prediction, pp. 492–495.*
Abaza et al, J of Protein Chemistry 11(5): 433–444, 1992.*
Barry et al, Archives of Biochemistry and Biophysics 300(1): 440–450, 1993.*
Ryder et al, J Chromatography 80: 128–132, 1973.*
Tanuma et al, Biochem. Biophysical Res. Communication 265: 395–399; 1999.*
Campbell et al, in Monoclonal Antibody Technology, 1984, Elsevier Science Publisher, New York, NY, p. 1–32.*
Barry et al., "Activation of Programmed Cell Death (Apoptosis) By Cisplatin, Other Anticancer Drugs, Toxins and Hyperthermia", *Biochem. Pharmacol.* 1990 40:2353–2362.
Sorenson et al., "Analysis of Events Associated With Cell Cycle Arrest $G_2$ Phase and Cell Death Induced by Cisplatin", *J. Natl Cancer Inst.* 1990 82:749–755.
Barry, M.A. and Eastman, A., "Identification of Deoxyribonuclease II as an Endonuclease Involved in Apoptosis[1,2]", *Archives of Biochem and Biophys.* 1993 300(1):440–450.
Cohen, J.J. and Duke, R.C., "Glucocorticoid Activation of a Calcium–Dependent Endonuclease in Thymocyte Nuclei Leads to Cell Death[1]", *J. Immunol.* 1984 132:38–42.

Eastman, A., "Deoxyribonuclease II in apoptosis and the significance of intracellular acidification", *Cell Death and Differentiation* 1994 1:7–9.
Kaufmann, S.H., "Induction of Endonucleolytic DNA Cleavage in Human Acute Myelogenous Leukemia Cells by Etoposide, Camptothecin, and Other Cytotoxic Anticancer Drugs: A Cautionary Note", *Cancer Res.* 1989 49:5870–5878.
Lennon et al., Induction of apoptosis (programmed cell death) in tumour cell lines by widely diverging stimuli, *Biochem. Soc. Trans.* 1990 18:343–345.
Enari, M. et al., "A caspase–activated DNase that degrades DNA during apoptosis, and its inhibitor ICAD", 1998 Nature 391:43–50.
McConkey et al., "Interleukin 1 Inhibits T Cell Receptor–mediated Apoptosis in Immature Thymocytes", *J. Biol. Chem.* 1990 265:3009–3011.
McConkey et al., "2,3,7,8–Tetrachlorodibenzo–p–dioxin Kills Immature Thymocytes by $Ca^{2+}$–Mediated Endonuclease Activation", *Science* 1988 242:256–259.
Peitsch et al., "Characterization of the endogenous deoxyribonuclease involved in nuclear DNA degradation during apoptosis (programmed cell death)", *EMBO J.* 1993 12:371–377.
Rodriquez–Tarduchy et al., "Regulation of apoptosis in interleukin–3–dependent hemopoietic cells by interleukin–3 and calcium ionophores", *EMBO J.* 1990 9:2997–3002.
Takano et al., "Apoptosis Induced by Mild Hyperthermia in Human and Murine Tumour Cell Lines: A Study Using Electron Microscopy and DNA Gel Electrophoresis", *J. Pathol.* 1991 163:329–336.
Torriglia, et al., "Involvement of DNase II in Nuclear Degeneration during Lens Cell Differentiation", *J. Biol. Chem.* 1995 270:28579–28585.
Wyllie, A.H., et al., "Cell Death: The Significance of Apoptosis", *Int. Rev. Cytol.* 1980 68:251–306.
Tanuma, S. and Shiokawa, D., "Cloning of a cDNA Encoding a Rat DNase II–like Acid DNase", *Biochemical and Biophysical Research Communications* 1999 285:395–399.
Shiokawa D. and Tanuma S., "DLAD, a novel mammalian divalent cation–independent endonuclease with homology to DNase II", *Nucleic Acids Res.* 1999 27 (20):4083–4089.

* cited by examiner

*Primary Examiner*—Christina Chan
*Assistant Examiner*—Phuong N. Huynh
(74) *Attorney, Agent, or Firm*—Licata & Tyrrell P.C.

(57) ABSTRACT

The present invention provides cDNAs encoding deoxyribonuclease IIβ and isolated, purified deoxyribonuclease IIβ proteins. Antibodies against this protein and antisense agents targeted to a cDNA or corresponding mRNA encoding deoxyribonuclease IIβ are provided. In addition, methods of identifying and using modulators of deoxyribonuclease IIβ activity are described.

1 Claim, No Drawings

US 6,767,997 B2

ANTIBODIES THAT BIND DEOXYRIBONUCLEASE IIβ ENZYME PROTEINS

This application is a continuation-in-part of U.S. patent application Ser. No. 09/541,840, filed Apr. 3, 2000, now issued as U.S. Pat. No. 6,350,723.

This invention was made in the course of research sponsored by the National Institutes of Health. The U.S. Government may have certain rights in this invention.

BACKGROUND OF THE INVENTION

Controlled cell death is critical for the life of a human; too much cell death can cause the symptoms of cystic fibrosis and also lead to diseases such a neurodegeneration and acquired immune deficiency syndrome (AIDS). In contrast, too little cell death can lead to cancer or autoimmune diseases. Recent studies have defined the pathway of cell death as "apoptosis" and have identified some of the biochemical steps involved.

Apoptosis is a homeostatic mechanism involved in the controlled death of obsolete cells during metamorphosis, differentiation, cell turnover, and hormone mediated deletion of thymocytes (Wyllie et al. *Int. Rev. Cytol.* 1980 68:251–306). Apoptosis has also been identified as the mechanism of cell killing during growth factor withdrawal (Rodriguez-Tarduchy et al. *EMBO J.* 1990 9:2997–3002; McConkey et al. *J. Biol. Chem.* 1990 265:3009–3011), T-cell deletion, treatment with many cytotoxic agents (Cohen, J. J. and Duke, R. C. *J. Immunol.* 1984 132:38–42; Barry et al. *Biochem. Pharmacol.* 1990 40:2353–2362; Kaufmann, S. H. *Cancer Res.* 1989 49:5870–5878; and McConkey et al. *Science* 1988 242:256–259), and following hyperthermia (Barry et al. *Biochem. Pharmacol.* 1990 40:2353–2362; Lennon et al. *Biochem. Soc. Trans.* 1990 18:343–345; Takano et al. *J. Pathol.* 1991 163:329–336).

Central to the mechanism of apoptosis is internucleosomal DNA digestion by endogenous endonucleases. Mammalian cells contain a variety of endonucleases which could be involved in internucleosomal DNA digestion. It was originally postulated that the primary endonuclease involved in apoptosis is a $Ca^{2+}/Mg^{2+}$-dependent endonuclease. Several $Ca^{2+}/Mg^{2+}$-dependent endonucleases have been identified, one of which is deoxyribonuclease I (DNase I), (Peitsch et al. *EMBO J.* 1993 12:371).

Recent experiments, however, indicate that DNase I may not be the primary endonuclease involved in apoptosis. It has been found that many cells do not contain this endonuclease. The role of DNase I, or any other $Ca^{2+}/Mg^{2+}$-dependent endonuclease is further unlikely, as often no increase or only a minor increase in $Ca^{2+}$ levels occurs in apoptotic cells (Eastman, A. *Cell Death and Differentiation* 1994 1:7–9).

An alternate endonuclease that is active below pH 7.0 and has no apparent requirement for $Ca^{2+}$ or $Mg^{2+}$ has been detected (Sorenson et al. *J. Natl. Cancer Inst.* 1990 82:749). This alternate endonuclease was identified as deoxyribonuclease II (DNase II; Barry, M. A. and Eastman, A. *Archives of Biochem and Biophys.* 1993 300(1):440–450). It was proposed that this enzyme is involved in the internucleosomal digestion or fragmentation of DNA which is one of the early steps in the pathway of apoptosis. Another report that has implicated DNase II in cell death involves lens fiber cell differentiation, a process where the cells lose their nuclei in a manner similar to apoptosis (Torriglia, A. et al. 1995 J. Biol. Chem. 270:28579–28585). In this process, the chromatin condenses and the cells degrade their genomic DNA. DNase II was found by immunocytochemistry to be localized in the cytoplasm but translocated to the nucleus of the fiber cell before degeneration. These findings implicate DNase II as the endonuclease responsible for genomic degradation observed during lens nuclear degeneration, and further support a role for this enzyme in mechanisms of cell death.

However, more recent results have implicated yet another endonuclease, referred to CAD or caspase-activated deoxyribonuclease, in apoptosis (Enari, M. et al. 1998 *Nature* 391:43–50). Thus, it remains to be determined which specific endonuclease is involved in apoptosis, The enzyme referred to herein as deoxyribonuclease IIα (DNA IIα) was isolated and purified and the amino acid sequence determined (PCT/US97/18262). The DNA sequences for both the human and bovine proteins of DNase IIα have also been cloned (PCT/US97/18262). Use of DNA IIα in alleviating the suffering in patients with cystic fibrosis is also disclosed in this PCT application.

In cystic fibrosis, the lungs of patients fill with the remnants of dead cells, and in particular with the DNA from these dead cells. The presence of DNA makes the mucous plugs too viscous to expel. A suggested therapy for these symptoms is the use of DNase I to digest the DNA, thereby permitting expulsion of the mucous plugs. However, this therapy has not been particularly effective due to inactivity of the DNase I enzyme in the presence of actin, also present in the sputum.

It is believed that DNase II enzymes and variations thereof may provide a more effective therapeutic alternative.

Another isoform of the DNase II enzyme, referred to herein as deoxyribonuclease IIβ (DNase IIβ) has now been identified and the gene and protein sequences for the mouse and human homolog have been determined.

SUMMARY OF THE INVENTION

An object of the present invention is to provide a cDNA encoding deoxyribonuclease IIβ.

Another object of the present invention is to provide an isolated, purified deoxyribonuclease IIβ enzyme.

Yet another object of the present invention is to provide antibodies against this protein which can be used in diagnosing cells at various stages in the apoptotic pathway.

Yet another object of the present invention is to provide antisense agents targeted to a cDNA or corresponding mRNA encoding deoxyribonuclease IIβ.

Yet another object of the present invention is to provide a method for identifying agents that inhibit DNase IIβ activity comprising treating cells with a test agent, transfecting cells with DNase IIβ, maintaining said transfected cells in culture, and monitoring apoptosis in treated and untreated cells to determine whether the test agent modulates apoptosis.

Yet another object of the present invention is to provide a method for inducing apoptosis in selected cells comprising transfecting cells with a vector expressing the DNase IIβ cDNA so that apoptosis is induced.

Yet another object of the present invention is to provide a method of digesting DNA released from dead cells with an effective amount of an isolated, purified DNase IIβ protein so that DNA is digested.

DETAILED DESCRIPTION OF THE INVENTION

The existence of a deoxyribonuclease II (DNase II) enzyme as a protein of lysosomal origin that is involved in cellular digestion of foreign DNA has been known for many years. Recently, a DNase II enzyme has been linked with the DNA fragmentation that occurs at an early stage in apoptosis. The bovine and human forms of this DNase II protein, referred to herein as DNase IIα protein have been isolated and purified and the amino acid sequences of these proteins are disclosed in PCT/US97/18262. cDNAs encoding the bovine and human form of DNase IIα have also been cloned and characterized in PCT/US97/18262.

An isoform of this enzyme, referred to herein as deoxyribonuclease IIβ (DNase IIβ) has now been identified.

This full length gene for this isoform was first identified in mice by sequence comparison to expressed sequence tags entered in Genbank database which were similar, but not identical to DNase IIα. Oligonucleotide primers were synthesized to obtain the complete DNase IIβ mouse gene. The mouse DNase IIβ cDNA sequence is depicted as SEQ ID NO:1. The protein sequence of mouse DNase IIβ is depicted in SEQ ID NO:2.

Information from the mouse sequence was used to isolate a human homolog of this gene. The human DNase IIβ cDNA sequence is depicted as SEQ ID NO:3. The protein sequence of human DNase IIβ encoded by the cDNA of SEQ ID NO:3 is depicted in SEQ ID NO:4.

Mouse and rat cDNAs of this homolog of DNase IIα have also been disclosed recently by Shiokawa and Tanuma (*Nucleic Acid Res.* 1999 27(20):4083–4089 and *Biochemical and Biophysical Research Communications* 1999 285:395–399).

It has been found that the DNase IIβ protein, like the DNase IIα protein, retains a critical histidine in the predicted active site thus indicating that these proteins have similar activities. However, there is sufficient difference in the region surrounding this histidine to suggest that their activities, and in particular their potential as a therapeutic for cystic fibrosis, may be slightly different. Specifically, the predicted active site of human DNase IIα is FNSTEDHSKWCV (SEQ ID NO:5) while the equivalent sequence in the human DNase IIβ isoform is FSSYQDHAKWCI (SEQ ID NO:6).

Further, it has now been found that DNase IIβ is expressed at high levels in human salivary glands and is secreted into the saliva.

Using fluorescence in situ hybridization (FISH), it has now been determined that the human DNase IIβ is located at chromosome 1p22. Chromosome 1p22 is frequently a lost or rearranged region in numerous types of cancer including breast, lymphoma, liver and mesothelioma. While several genes in this region have been investigated, no clear candidate for the tumor suppressor at this locus has been identified. DNase IIα is lethal when reintroduced into cells. Based on sequence similarity, it is expected that its isomer DNase IIβ will have similar activity. Since this cell killing activity is consistent with the function of tumor suppressor genes, it is believed that DNase IIβ could represent the tumor suppressor that is lost in these types of tumors. Accordingly, the mouse and human DNase IIβ gene sequence and protein of the present invention are believed to be useful in the development of assays, screening approaches and targeted therapies for cancer.

For example, polymerase chain reaction (PCR) techniques can be used to determine whether the gene is missing or mutated in cancer cells. Such cells are expected to be more susceptible to the introduction of foreign genes through means such as gene therapy.

Identification of agents which increase DNase IIβ expression are expected to be useful in suppressing tumor formation and/or inducing apoptosis in cells. Inducing apoptosis is not only useful in treatment of cancer, but also in the treatment of various autoimmune disorders such as multiple sclerosis in which immune cells that recognize the normal patient tissue have failed to die as should normally happen.

The mouse and human DNase IIβ gene sequence and protein of the present invention are also useful in the development of agents which decrease expression of endogenous DNase IIβ in cells. For example, antisense agents targeted to a portion of the cDNA sequence of the present invention or the corresponding mRNA can be developed. These antisense agents can then be used to decrease or inhibit the expression of DNase IIβ thereby protect cells from premature death. These antisense agents may therefore be useful in treating diseases resulting from too much cell death such as neurodegeneration and AIDS.

Accordingly, cDNAs of the present invention are useful in identifying agents which modulate, i.e., increase or decrease, apoptosis in cells. In this method, cells from a single culture are divided in two groups. The first group, referred to as the treated cells, are placed in contact with a test agent in a vehicle. The second group, referred to as untreated cells, are placed in contact with vehicle only. Treated and untreated cells are then transfected with the cDNA of the present invention and apoptosis in the treated and untreated cells is monitored to determine whether treating cells with the test agent modulates apoptosis in the cells.

In addition, the DNase IIβ proteins of the present invention or fragments thereof are useful as antigens to produce antibodies thereto. By "antibody" it is meant to include, but is not limited to, both polyclonal and monoclonal antibodies as well as chimeric, single chain, and humanized antibodies along with Fab fragments, or the product of a Fab expression library. Various techniques for producing such antibodies are well known in the art.

Polyclonal antibodies generated against DNase IIβ can be obtained by direct injection of the isolated, purified proteins of the present invention or fragments thereof into an animal, preferably a nonhuman. Such antibodies can then be used to isolate the enzyme from tissues expressing that enzyme.

For preparation of monoclonal antibodies, any technique which provides antibodies produced by continuous cell line cultures can be used. Such techniques are used routinely by those skilled in the art. Some examples include, but are not limited to, the hybridoma technique, the trioma technique, the human B-cell hybridoma technique and the EBV-hybridoma technique.

These antibodies are useful in studying the expression of DNase IIβ in a variety of cells. DNase IIβ levels can be determined in selected cells by contacting selected cells with the antibody against DNase IIβ and detecting binding of antibody to deoxyribonuclease IIβ enzyme in the selected cells. For example, in one embodiment, an antibody of the present invention is used to detect the intact protein in normal human cells compared to tumor cells to determine whether the tumor cells fail to express the endonuclease.

DNase IIα digests DNA. Thus, given the similarity between DNase IIα and the IIβ isoform of the present invention, it is believed that DNase IIβ will also digest DNA. Patients suffering from cystic fibrosis have viscous sputum in their lungs; accumulation of this viscous sputum can lead to suffocation. Much of this viscosity comes from the release of DNA from cells dying in the lungs. DNase I is currently used in patients with cystic fibrosis as an inhaler to digest DNA in the mucous plugs of the lungs of these patients. However, this enzyme is inhibited by actin, also present in sputum. Thus, the efficacy of this treatment is limited. Previously, DNase II enzymes would not have been considered a practical alternative because enzymatic activity was only observed at a pH below that of the lungs. However, the low pH activity of DNase IIα is associated with a small DNase II fragment rather than the full length protein. The full length DNA IIα and DNA IIβ identified herein may have other catalytic activities such as an ability to digest DNA at higher pH. Accordingly, it is believed that administration of a concentration of a DNase II enzyme which causes digestion of DNA in sputum will be effective in alleviating suffering of patients with cystic fibrosis by decreasing the viscosity of the sputum in the lungs.

The following nonlimiting examples are provided to further illustrate the present invention.

EXAMPLES

Example 1

Identification of Expressed Sequence Tags

The cDNA sequence of DNase IIα was submitted to the Genbank database on a regular basis for analysis against the rapidly accumulating data deposited therein to identify other cDNA and protein sequences with similarity to DNase IIα. An expressed sequence tag (EST) from mouse cDNA was identified that has high similarity to DNase IIα. These EST sequences are random pieces of cDNA that have been partially sequence but have no known function. The identified mouse EST was purchased and completely sequenced. This sequencing revealed a complete cDNA sequence with considerable homology to DNase IIα, but with sufficient differences that it obviously represented a different gene.

Additional EST sequences from human tissues were found that had similarity to this mouse EST. However, upon sequencing they contained incomplete sequences. Specifically, EST # AI420898, whose sequence was deposited into Genbank on Mar. 28, 1999 was found to contain 932 bp of the gene referred to herein now as DNase IIβ. This sequence was cloned into pT7T3D-Pac vector from Pharmacia.

Example 2

Nucleic Acid Sequencing

Plasmid DNA obtained in Example 1 was sequenced using the Big-DyeDeoxy Terminator Cycle Sequencing Kit from Applied Biosystems, followed by analysis on an Applied Biosystems 370 DNA automated sequencer.

Example 3

Genomic Localization

Human genomic DNA was used as a substrate for PCR using oligonucleotide primers predicted from the homology with DNase IIα to span intron 5 of DNase IIβ. A 2,000 base pair fragment was isolated and cloned into the PCR-script vector. This genomic fragment was biotinylated and used as a probe in fluorescent in situ hybridization to whole chromosomes. The probe hybridized to chromosome 1p22.

What is claimed is:

1. An antibody which specifically binds an isolated and purified deoxyribonuclease IIβ enzyme comprising SEQ ID NO:2 or SEQ ID NO:4.

* * * * *

SEQUENCE LISTING

<160> NUMBER OF SEQ ID NOS: 6

<210> SEQ ID NO 1
<211> LENGTH: 1224
<212> TYPE: DNA
<213> ORGANISM: Mus sp.

<400> SEQUENCE: 1

```
tcccagtccc ctgcatggaa tgaaggccac agatagaaaa tgacagcaaa gcctctaaga      60
acagttcttt ctttgctctt ctttgccctc tctggggtcc tggggacacc agaaatctca     120
tgcagaaatg aatatggtga agctgtggac tggtttatct tttataagtt acccaaaagg     180
actagcaagg caagtgaaga ggcggggctg cagtacctgt acctggactc cacaagacaa     240
acctggaaca agagcctcta cctgattaac agcaccagga gtgctctggg gaggacctta     300
cagcatctgt atgacacaca taattccacg aatgacacag cctatctaat atacaacgat     360
ggtgtccctg gatctgtgaa ttacagcaga cagtatggac atgccaaagg tctgctggta     420
tggaacagaa cgcagggggtt ctggctgata cactctgttc ccaagtttcc cccagttcat     480
ggctatgagt acccaacctc ggggaggcga tatggacaaa ccggcatctg catcactttc     540
ggatacagcc agtttgagga aatagatttt cagctcttgg tcttacaacc aaacatctac     600
agctgcttca ttccaagcac ctttcactgg aaacttatct acatgccccg gatgtgtgcc     660
aactccagtt ccttaaagat ccctgtccgg tacctcgctg aactgcactc agcccagggt     720
ctaaacttcg tccattttgc aaaatcaagt ttttatactg atgacatctt tacaggatgg     780
atagctcaaa agttgaagac acatttgtta gcacaaacct ggcagaaaaa gaaacaagag     840
```

-continued

```
cttccttcaa actgttccct gccttaccat gtctacaaca tcaagtccat tggggtaact    900
tccaagtctt acttcagttc tcgccaagac cattccaaat ggtgtgtttc cataaagggc    960
tccgcaaatc gctggacctg cattggagac ctaaatcgaa gcctacacca agccttaaga   1020
ggtggaggat tcatctgtac aaagaatcac tacatttacc aggcatttca taaattatat   1080
ctccgttatg ggttctgtaa gtaaactcgg tgaaaggcca caccctctgt ccttgaaaac   1140
actggcactg aacatctcg ccttggatct gttctccata atatcaaggc ttctgagtga   1200
gcacaacgta gcgtccaata aaag                                         1224
```

<210> SEQ ID NO 2
<211> LENGTH: 354
<212> TYPE: PRT
<213> ORGANISM: Mus sp.

<400> SEQUENCE: 2

```
Met Thr Ala Lys Pro Leu Arg Thr Val Leu Ser Leu Leu Phe Phe Ala
 1               5                  10                  15

Leu Ser Gly Val Leu Gly Thr Pro Glu Ile Ser Cys Arg Asn Glu Tyr
                20                  25                  30

Gly Glu Ala Val Asp Trp Phe Ile Phe Tyr Lys Leu Pro Lys Arg Thr
            35                  40                  45

Ser Lys Ala Ser Glu Glu Ala Gly Leu Gln Tyr Leu Tyr Leu Asp Ser
        50                  55                  60

Thr Arg Gln Thr Trp Asn Lys Ser Leu Tyr Leu Ile Asn Ser Thr Arg
 65                  70                  75                  80

Ser Ala Leu Gly Arg Thr Leu Gln His Leu Tyr Asp Thr His Asn Ser
                85                  90                  95

Thr Asn Asp Thr Ala Tyr Leu Ile Tyr Asn Asp Gly Val Pro Gly Ser
            100                 105                 110

Val Asn Tyr Ser Arg Gln Tyr Gly His Ala Lys Gly Leu Leu Val Trp
        115                 120                 125

Asn Arg Thr Gln Gly Phe Trp Leu Ile His Ser Val Pro Lys Phe Pro
130                 135                 140

Pro Val His Gly Tyr Glu Tyr Pro Thr Ser Gly Arg Arg Tyr Gly Gln
145                 150                 155                 160

Thr Gly Ile Cys Ile Thr Phe Gly Tyr Ser Gln Phe Glu Glu Ile Asp
                165                 170                 175

Phe Gln Leu Leu Val Leu Gln Pro Asn Ile Tyr Ser Cys Phe Ile Pro
            180                 185                 190

Ser Thr Phe His Trp Lys Leu Ile Tyr Met Pro Arg Met Cys Ala Asn
        195                 200                 205

Ser Ser Ser Leu Lys Ile Pro Val Arg Tyr Leu Ala Glu Leu His Ser
210                 215                 220

Ala Gln Gly Leu Asn Phe Val His Phe Ala Lys Ser Ser Phe Tyr Thr
225                 230                 235                 240

Asp Asp Ile Phe Thr Gly Trp Ile Ala Gln Lys Leu Lys Thr His Leu
                245                 250                 255

Leu Ala Gln Thr Trp Gln Lys Lys Gln Glu Leu Pro Ser Asn Cys
            260                 265                 270

Ser Leu Pro Tyr His Val Tyr Asn Ile Lys Ser Ile Gly Val Thr Ser
        275                 280                 285

Lys Ser Tyr Phe Ser Ser Arg Gln Asp His Ser Lys Trp Cys Val Ser
290                 295                 300
```

Ile Lys Gly Ser Ala Asn Arg Trp Thr Cys Ile Gly Asp Leu Asn Arg
305                 310                 315                 320

Ser Leu His Gln Ala Leu Arg Gly Gly Phe Ile Cys Thr Lys Asn
            325                 330                 335

His Tyr Ile Tyr Gln Ala Phe His Lys Leu Tyr Leu Arg Tyr Gly Phe
            340                 345                 350

Cys Lys

<210> SEQ ID NO 3
<211> LENGTH: 1268
<212> TYPE: DNA
<213> ORGANISM: Homo sapiens

<400> SEQUENCE: 3

```
atggggaaag tgtcctgctg tggcatgaaa taaatgaaac agaaaatgat ggcaagactg     60
ctaagaacat cctttgcttt gctcttcctt ggcctctttg gggtgctggg ggcagcaaca    120
atttcatgca gaaatgaaga agggaaagct gtggactggt ttactttta aagttacct     180
aaaagacaaa acaaggaaag tggagagact gggttagagt acctgtacct agactctaca   240
actagaagct ggaggaagag tgagcaacta atgaatgaca ccaagagtgt tttgggaagg   300
acattacaac agctatatga agcatatgcc tctaagagta acaacacagc ctatctaata   360
tacaatgatg gagtccctaa acctgtgaat tacagtagaa agtatggaca caccaaaggt   420
ttactgctgt ggaacagagt tcaagggttc tggctgattc attccatccc tcagtttcct   480
ccaattccgg aagaaggcta tgattatcca cccacaggga gacgaaatgg acaaagtggc   540
atctgcataa cttcaagta caaccagtat gaggcaatag attctcagct cttggtctgc   600
aaccccaacg tctatagctg ctccatccca gccaccttc accaggagct cattcacatg   660
ccccagctgt gcaccagggc cagctcatca gagattcctg caggctcct caccacactt   720
cagtcggccc agggacaaaa attcctccat tttgcaaagt cggattcttt tcttgacgac   780
atctttgcag cctggatggc tcaacggctg aagacacact tgttaacaga acctggcag   840
cgaaaaagac aagagcttcc ttcaaactgc tcccttcctt accatgtcta caatataaaa   900
gcaattaaat tatcacgaca ctcttatttc agttcttatc aagatcacgc caagtggtgt   960
atttcccaaa agggcaccaa aaatcgctgg acatgtattg gagacctaaa tcggagtcca  1020
caccaagcct tcagaagtgg aggattcatt tgtacccaga attggcaaat ttaccaagca  1080
tttcaaggat tagtattata ctatgaaagc tgtaagtaaa cttggtgaaa ggacacaggt  1140
actatcattg aaaaccttga caatgggtct tcttccatta caccttcttt atatttaaa   1200
ggcctgtgaa tatacttata acctgcatat cacaaaataa aacatatttc tctcatgttt  1260
accattta                                                            1268
```

<210> SEQ ID NO 4
<211> LENGTH: 357
<212> TYPE: PRT
<213> ORGANISM: Homo sapiens

<400> SEQUENCE: 4

Met Met Ala Arg Leu Leu Arg Thr Ser Phe Ala Leu Leu Phe Leu Gly
1               5                   10                  15

Leu Phe Gly Val Leu Gly Ala Ala Thr Ile Ser Cys Arg Asn Glu Glu
            20                  25                  30

Gly Lys Ala Val Asp Trp Phe Thr Phe Tyr Lys Leu Pro Lys Arg Gln

-continued

```
                35                  40                  45
Asn Lys Glu Ser Gly Glu Thr Gly Leu Glu Tyr Leu Tyr Leu Asp Ser
 50                  55                  60

Thr Thr Arg Ser Trp Arg Lys Ser Glu Gln Leu Met Asn Asp Thr Lys
 65                  70                  75                  80

Ser Val Leu Gly Arg Thr Leu Gln Gln Leu Tyr Glu Ala Tyr Ala Ser
                 85                  90                  95

Lys Ser Asn Asn Thr Ala Tyr Leu Ile Tyr Asn Asp Gly Val Pro Lys
                100                 105                 110

Pro Val Asn Tyr Ser Arg Lys Tyr Gly His Thr Lys Gly Leu Leu Leu
                115                 120                 125

Trp Asn Arg Val Gln Gly Phe Trp Leu Ile His Ser Ile Pro Gln Phe
130                 135                 140

Pro Pro Ile Pro Glu Glu Gly Tyr Asp Tyr Pro Pro Thr Gly Arg Arg
145                 150                 155                 160

Asn Gly Gln Ser Gly Ile Cys Ile Thr Phe Lys Tyr Asn Gln Tyr Glu
                165                 170                 175

Ala Ile Asp Ser Gln Leu Leu Val Cys Asn Pro Asn Val Tyr Ser Cys
                180                 185                 190

Ser Ile Pro Ala Thr Phe His Gln Glu Leu Ile His Met Pro Gln Leu
                195                 200                 205

Cys Thr Arg Ala Ser Ser Glu Ile Pro Gly Arg Leu Leu Thr Thr
210                 215                 220

Leu Gln Ser Ala Gln Gly Gln Lys Phe Leu His Phe Ala Lys Ser Asp
225                 230                 235                 240

Ser Phe Leu Asp Asp Ile Phe Ala Ala Trp Met Ala Gln Arg Leu Lys
                245                 250                 255

Thr His Leu Leu Thr Glu Thr Trp Gln Arg Lys Arg Gln Glu Leu Pro
                260                 265                 270

Ser Asn Cys Ser Leu Pro Tyr His Val Tyr Asn Ile Lys Ala Ile Lys
                275                 280                 285

Leu Ser Arg His Ser Tyr Phe Ser Ser Tyr Gln Asp His Ala Lys Trp
                290                 295                 300

Cys Ile Ser Gln Lys Gly Thr Lys Asn Arg Trp Thr Cys Ile Gly Asp
305                 310                 315                 320

Leu Asn Arg Ser Pro His Gln Ala Phe Arg Ser Gly Gly Phe Ile Cys
                325                 330                 335

Thr Gln Asn Trp Gln Ile Tyr Gln Ala Phe Gln Gly Leu Val Leu Tyr
                340                 345                 350

Tyr Glu Ser Cys Lys
                355

<210> SEQ ID NO 5
<211> LENGTH: 12
<212> TYPE: PRT
<213> ORGANISM: Homo sapiens
```

-continued

```
<400> SEQUENCE: 5

Phe Asn Ser Thr Glu Asp His Ser Lys Trp Cys Val
  1               5                  10

<210> SEQ ID NO 6
<211> LENGTH: 12
<212> TYPE: PRT
<213> ORGANISM: Homo sapiens

<400> SEQUENCE: 6

Phe Ser Ser Tyr Gln Asp His Ala Lys Trp Cys Ile
  1               5                  10
```